United States Patent [19]

Waknine

[11] Patent Number: 4,544,359

[45] Date of Patent: Oct. 1, 1985

[54] DENTAL RESTORATIVE MATERIAL

[75] Inventor: Samuel Waknine, Wallingford, Conn.

[73] Assignee: Pentron Corporation, Wallingford, Conn.

[21] Appl. No.: 677,595

[22] Filed: Dec. 3, 1984

Related U.S. Application Data

[63] Continuation-in-part of Ser. No. 570,366, Jan. 13, 1984, abandoned.

[51] Int. Cl.$^4$ .................................................. A61K 6/08
[52] U.S. Cl. ............................... 523/115; 260/998.11; 433/201.1; 433/202.1; 433/228.1; 523/115; 523/116; 523/117; 433/199.1
[58] Field of Search ............... 433/199, 201, 202, 228; 523/115, 116, 117; 260/998.11

[56] References Cited

U.S. PATENT DOCUMENTS

| | | | |
|---|---|---|---|
| 3,066,112 | 11/1962 | Bowen | 260/41 |
| 3,808,170 | 4/1974 | Rogers | 260/42.53 |
| 4,020,557 | 5/1977 | Rockett et al. | 32/15 |
| 4,032,504 | 6/1977 | Lee et al. | 260/42.18 |
| 4,150,012 | 4/1979 | Joos | 260/42.15 |
| 4,224,023 | 9/1980 | Cheung | 433/216 |
| 4,271,057 | 6/1981 | Drake et al. | 260/29.6 M |
| 4,281,991 | 8/1981 | Michl | 433/202 |
| 4,297,266 | 10/1981 | Ibsen et al. | 260/42.14 |
| 4,376,835 | 3/1983 | Schmitt et al. | 523/116 |
| 4,388,069 | 6/1983 | Orlowski | 433/228 |

FOREIGN PATENT DOCUMENTS

| | | | |
|---|---|---|---|
| 1128229 | 7/1982 | Canada | 400/77 |
| 1128230 | 7/1982 | Canada | 400/77 |
| 1488403 | 10/1977 | United Kingdom | |

*Primary Examiner*—Lorenzo B. Hayes
*Attorney, Agent, or Firm*—Barry Kramer

[57] ABSTRACT

In a dental restorative material comprising 20-30% by weight of a visible light polymerizable methacrylic ester monomeric system, from about 65-79% by weight of an inorganic filler and from about 1-5% by weight of collidal fumed silica; said inorganic filler having an average particle size diameter ranging from about 0.5 to 5 microns and said collidal fumed silica having an average particle size ranging from about 0.01 to about 0.05 micron, the improvement comprising subjecting the filler to a series of milling steps comprising (1) wet milling in aqueous medium having a pH of 5-7; (2) surface etch milling in an aqueous etchant medium and (3) a silanizing milling in a silane solution.

19 Claims, 5 Drawing Figures

DENTAL RESTORATIVE MATERIAL

This application is a continuation-in-part of copending application Ser. No. 570,366 filed Jan. 13, 1984, now abandoned.

This invention relates to an improved dental restorative composition. More particularly, this invention relates to an improved dental restorative material comprising a visible light-curable organic binder and particles of an inorganic filler dispersed therein.

Historically, the dental profession has used several different types of materials for restorative dental purposes. Unfilled acrylic resins were initially used for such purposes. Acrylics, however, exhibited high coefficients of thermal expansion, e.g., $80-100 \times 10^{-6}$ mm/mm/°C.; whereas, the coefficient of thermal expansion for vita tooth structure is about $11 \times 10^{-6}$ mm/mm°C. This disparity, coupled with high shrinkage upon polymerization, resulted in poor marginal adaptability ultimately leading to secondary decay. Moreover, the wear and abrasion characteristics as well as the overall physical, mechanical and optical properties were quite poor. Silicate cements were also used for restorative purposes. The silicate cements, however, exhibited poor long term stability, a tendency to discolor and were quite brittle thereby limiting the utilization of such materials.

Subsequently, direct filling resins were developed; however, these materials suffered from excessive shrinkage upon polymerization and poor thermal expansion characteristics. Dental composite materials comprising an inorganic filler component such as glass and an organic matrix component such as a polymerizable monomer have been available since as early as 1965. Such materials are particularly valuable when used to restore the appearance and function of teeth which have decayed, fractured, or otherwise become defective or unsightly. Such composite materials were developed largely through the efforts of R. L. Bowen (see, for example, U.S. Pat. No. 3,066,112; R. L. Bowen et al, "Composite Restorative Materials", paper given at 50th Anniversary Symposium on Dental Material Research, NBS, Oct. 6–8, 1969). Such composites generally involve the use of an acrylic or methacrylic based system in which a silica or silicate glass filler is covalently bonded to a resin matrix, or to a coupling agent which is covalently bonded to both. With fillers used to the 70–80 weight percent level, polymerization shrinkage and thermal expansion are greatly reduced in comparison with the unfilled direct filling resins which have been previously employed. Despite the advantages of such ceramic reinforced polymeric matrix composites as compared to earlier silicate cements and direct filling resins, such composites have not been entirely satisfactory from the standpoint of resistance to abrasion and wear, ease of finishing and ease of implacement.

The fillers initially employed in dental composite materials were of a particle size ranging from about 5 to about 150 microns and were used in large amounts up to about 80% by weight of the total composition. It was found that use of such large particle size fillers resulted in rather poor mechanical properties especially, low diametral tensile strength. In addition, such compositions were very difficult to polish resulting in a relatively rough finish and frequently exhibited insufficient translucency to permit good blending of the restored tooth with adjacent teeth.

In order to overcome the deficiencies inherent in the use of such large particle size fillers, various manufacturers have recently placed on the market "microfilled" composites in which part of the filler in the form of colloidal silica having an average particle size of about 40 millimicrons prepolymerized in an organic polymeric matrix was admixed with a glass filler having a particle size ranging from about 5–10 microns. However, when using these relatively ultrafine particle sized fillers, only about 25 to 50% of the composite can be filler. This resulted in the overall composite exhibiting much greater shrinkage upon polymerization than the prior composites using large particle size filler, so that such composites tend to pull away from the teeth upon curing. Such "microfilled" composites, while exhibiting high polishability, were also of substantially lower diametral tensile strength than the earlier composites. Moreover, such composites have also exhibited higher coefficients of thermal expansion and higher water absorption than those of the prior composites containing larger sized particles.

Accordingly, it is an object of the present invention to provide a composite dental material which overcomes the deficiencies and disadvantages previously associated with composites using large-particle sized fillers or microfilled composites.

It is another object of the present invention to provide a composite dental material exhibiting high diametral tensile strength, X-ray opacity, excellent optical properties, excellent polishibility, low water absorption and full compliance with the requirements of the American Dental Association Specification No. 27.

These as well as other objects and advantages are accomplished by the improved dental restorative material of the present invention which comprises from about 20 to 30% by weight of a visible-light polymerizable methacrylic ester monomeric system, from about 65 to 79% by weight of an inorganic filler prepared by wet milling, milling in an aqueous etchant medium and a silanizing milling, and from about 1 to 5% by weight of colloidal fumed silica; said inorganic filler having an average particle size diameter ranging from about 0.5 to 5 microns and said fumed silica having an average particle size ranging from about 0.01 to about 0.05 micron.

It has been found in accordance with the present invention that by subjecting the inorganic filler to a specific series of milling and treating operations, a combination of high diametral tensile strength and high polishibility can be achieved in the filled composite resin system as compared to prior composite dental materials employing either large particle size or submicron size fillers.

The present invention will be more clearly understood and the novel structure of the inorganic filler employed in the present invention, which structure is related to the milling techniques employed in the preparation thereof, will be more readily appreciated by reference to the accompanying drawing wherein.

The composite dental material of the present invention comprises a unique inorganic filler having an average particle size diameter of from about 0.5 to 5 microns homogeneously dispersed in an organic visible-light polymerizable monomeric matrix. In addition, a relatively small amount of fumed silica is also dispersed within the monomeric matrix. The inorganic filler primarily comprises an X-ray opaque alkali metal or alkaline earth metal silicate such as lithium silicate, barium silicate and the like. For purposes of illustration, and as the preferred silicate species, barium silicate will hereinafter be employed as being typical of the alkali metal or alkaline earth metal silicates which can be suitably employed in the present invention. The barium silicate exhibits substantially the same index of refraction as that of the organic monomeric matrix in which it is dispersed. The filler additionally contains a relatively small amount of borosilicate glass which imparts greater compressive strength to the resulting composite and enhances the translucency thereof thereby enabling better blending of the restorative material with the adjacent teeth. In addition, the presence of the borosilicate glass helps narrow the gap between the refractive indices of the barium silicate and the organic monomeric matrix.

The ability to provide a composite dental material exhibiting both high diametral tensile strength and high polishability is achieved in accordance with the present invention by the method by which the inorganic filler is prepared. This method involves a sequence of milling operations which includes wet milling to reduce the barium silicate and borosilicate to the requisite particle size and assure a very narrow particle size distribution and to uniformly disperse the borosilicate glass particles throughout the bulk of the barium silicate. Thereafter, the wet milled filler is subject to a further milling operation to etch the surface thereof which surprisingly has been found to impart a dramatic increase to the diametral tensile strength of the resulting composite. Subsequently, the so treated filler is subjected to a final milling operation during which it is silanized in order to render it compatible with the resin in which it will ultimately be dispersed.

The following detailed discussion will set forth methods by which the inorganic filler can be prepared, the visible-light polymerizable methacrylic ester monomer system can be prepared, the preparation of the ultimate composite dental material and the procedure by which the composite material is used to effect dental restoration.

INORGANIC FILLER PREPARATION

(i) wet milling

The inorganic filler of the present invention ultimately comprises a mixture of from about 5-20% by weight of borosilicate glass and from about 80-95% by weight barium silicate, said filler having an average particle size diameter of from about 0.5 to 5 microns.

Any conventional wet milling operation can be employed to reduce the required mixture to within the desired particle size diameter range. It is considered important to prepare the mixture by a series of wet milling operations since dry milling will result in fracture of the particles with a resultant undesirable coarseness and angularity imparted to the final milled filler particles which will adversely affect the polishability of the resulting composite system.

Thus, in one embodiment, the requisite quantities of barium silicate and borosilicate glass, each having a particle size distribution of from about 2-20 microns are loaded into a suitable grinding vessel. The vessel is filled to from $\frac{1}{2}-\frac{3}{4}$ its volume with a suitable grinding medium. The grinding medium can comprise any low alumina, low contaminant-generating substance such as porcelain balls, stainless steel balls, borosilicate glass rods and the like. The remaining volume of the container is filled with an aqueous medium having a pH of about 5-7. The container is sealed and the contents milled and/or ground for about 8-48 hours. If borosilicate glass rods are employed as the grinding medium, sufficient borosilicate glass is abraded off the rods during the grinding operation to obviate the need to initially add borosilicate glass at the commencement of the wet milling operation. Care should be taken to avoid the introduction of any contaminants to the system either by way of the grinding medium or the aqueous medium since contaminants can give rise to cross reactions with the polymerization system imparting discoloration to the final product.

Upon completion of the wet milling operation, the barium silicate is ground to an average particle size diameter ranging between about 3-8 microns. The borosilicate glass in the mixture ranges in particle size from about 2 to 5 microns.

Illustrative of the wet milling procedures which can be employed in the present invention, borosilicate glass rods are loaded into a 5 gallon glass carboy, until the carboy is half filled. The carboy is then filled with water, sealed and tumbled at 50-350 rpm for about 16-98 hours.

The resulting conditioned borosilicate glass rods are recovered and loaded into a grinding vessel, which is mounted for continuous combined oscillatory and vibratory motion, until the vessel is $\frac{3}{4}$ filled. Typically, about 2 to 5 kilograms of X-ray opaque barium silicate glass frit having a particle size distribution of from about 2-20 microns, preferably about 10 microns, is charged to the vessel and then, water is added to fill the vessel. The vessel is sealed and vibrated for about 8-48 hours whereupon the barium silicate frit is ground to an average particle size ranging between about 3-8 microns and sufficient borosilicate glass is abraded off the rods to provide the requisite barium silicate/borosilicate mixture.

Thereafter, the aqueous slurry of filler is recovered and progressively strained through 200, 400 and 600 mesh screens to remove any impurities or contaminants. The resulting filtrate is subjected to vacuum filtration. The resulting cake comprising an admixture of barium silicate frit and particles of borosilicate glass which have abraded off of the borosilicate glass rods during the wet milling process is dried in a convection oven at 120° C. for about 12-36 hours. The dried, milled filler is recovered and crushed with mortar and pestle to a fine powder.

Analysis establishes that the mixture resulting from wet milling employing the techniques described hereinabove comprises from about 5-20% by weight of borosilicate glass particles having an average particle size ranging from about 2 to 5 microns and from about 80–95% by weight of barium silicate glass particles having an average particle size ranging from about 3–8 microns.

(ii) milling with an aqueous etchant solution

It has been found critical in obtaining the high strength characteristics of the composite resin of the present invention that the filler obtained by wet milling undergo another milling step during which surface etching of the filler is effected.

Most conveniently, milling in an aqueous etchant generally can be effected as follows:

a glass or glass-lined carboy is filled to one-half its volume with borosilicate glass rods which have been conditioned as set forth hereinabove. Alternatively, low alumina, porcelain balls, stainless steel balls or another low alumina, non-contaminating grinding medium can be similarly employed.

From about 2 to 4 kilograms of the dried milled filler produced by wet milling as described hereinabove is charged to the carboy along with from about 4 to 8 liters of a clear, colorless aqueous solution of a material which will effect etching of glass, for example, bases such as NaOH, KOH, Ca(OH)$_2$, and the like; acids such as HCl, HF, and the like; and salts such as NaCl, KCl, and the like can be suitably employed. When acids are used, HF is the most preferred acid; however, certain precautions should be employed—the acid should be used in relatively dilute form, e.g., aqueous solutions containing from about 2–5% by weight of HF, and the carboy employed for further milling of the wet milled filler should be lines with an HF-resistant polymeric lining such as polyethylene or preferably, polypropylene. When bases are employed, it is considered preferable to buffer the solution to maintain a stable pH. Useful buffering agents include acetate, borate, phosphate, orothophosphate salts, and the like.

Preferably, a solution of sodium hydroxide (NaOH) buffered with mono-hydrogen sodium orthophosphate (Na$_2$HPO$_4$) and exhibiting a pH ranging from about 10–13 is employed in the etching-milling operation. A surprising increase in diametral tensile strength is imparted to the final light cured composite resin by subjecting the wet milled resin to the instant etching-milling step, especially when a base is employed under the most preferred pH conditions.

The loaded carboy is sealed and tumbled at 50–350 rpm for 2–8 hours. Thereafter, the resulting milled filler is separated from the milling medium and vacuum filtered. The filter cake is continuously washed with water until pH indicators in the filtrate indicate that neutrality (5.5–7.0) has been essentially attained. The recovered filter cake is then dried in a convection oven at 120° C. for 24 hours.

It is considered important that the filter cake be essentially neutralized since any acidity or alkalinity in the final filler will impart discoloration to the ultimate resin composite:

The neutralized filter cake is then crushed to a fine powder with a mortar and pestle.

(iii) silanizing milling

In order for the inorganic filler to be compatible with the organic polymeric matrix, it is necessary to silanate the inorganic filler. Silanization can be effected in accordance with the present invention by once again filling a glass or glass-lined carboy to one-half its volume with conditioned borosilicate glass rods, low alumina porcelain balls, stainless steel balls or other low alumina, non-contaminating grinding medium, adding thereto from about 5 to 7 kilograms and preferably, about 6 kilograms of a solution containing from about 5 to 10 weight percent, preferably about 8% by weight, silane (SiH$_4$) in methanol; and further adding thereto from about 2 to 5 kilograms, preferably about 3 kilograms of the milled filler recovered from the controlled pH milling step. The carboy is sealed and tumbled for about 4–8 hours at 50–350 rpm. Thereafter, the slurry of silanized filler is recovered from the carboy and subjected to vacuum filtration. The resulting filter cake is dried in a vacuum oven for one hour at 120° C. or alternatively, for 1–4 hours at 60° C. and then crushed by mortar and pestle giving rise to silanized filler particles having an average particle size diameter ranging from about 0.5 to 5 microns and preferably ranging from about 1.5 to 2.5 microns. Silanization results in from about 1.5 weight % silane preferably 2.0–2.5% silane, being coupled to the filler particles, based on total filler weight as determined by an ashing/burnout test at 800° C. for two hours.

It is important to maintain close control over the filler average particle size. If the average particle size is lower than about 1 micron, the filler becomes too opaque and loses the translucency required to make it aesthetically compatible with the ultimate organic resin matrix. If the average particle size is higher than about 5 microns, the filler particles can separate from the ultimate organic resin matrix resulting in decreased strength of the overall composite.

Thus, the inorganic filler of the present invention comprises a mixture of from about 5–20% borosilicate and from about 80–95% barium silcate, said filler having an average particle size diameter of from 0.5 to about 5 microns and containing from about 1.5 to 6% silane coupled thereto, said inorganic filler having been prepared by wet milling, further milling with an aqueous etchant solution and a silanizing milling.

ORGANIC MONOMER MATRIX PREPARATION

Any non-toxic organic monomer useful in dental composite restorative compositions can be employed in conjunction with the inorganic fillers of the present invention. The most commonly employed monomers are generally monomeric methacrylic esters. Because of an excellent combination of physical properties, i.e., diametral tensile strength, water sorption, index of refraction, shrinkage, and lack of toxicity and/or biocompatibility, most commercialy available dental composite resins are based on use of a cross-linking monomer or polymer such as methacrylates, polyurethanes and the like. Preferably, the monomeric reaction product of 4,4'-isopropylidenediphenol and glycidyl methacrylate, commonly referred to as "BIS-GMA" or derivatives thereof are employed. Other suitable cross-linking monomers or polymers include hydroxyethoxy methacrylate the reaction product of 4-methacryoyloxyethyl trimellitc anhydride and tributyl borane, ethoxylated bisphenol-A dimethacrylate, the addition product of N-phenylglycine and glycidyl methacrylate, the addition product of N-tolylglycine and glycidyl methacrylate, the addition product of pyromellitic dianhydride and 2-hydroxyethyl methacrylate, polyurethane methacrylate and other urethane polymers and the like.

Additionally, other monomethacrylate, dimethacrylate, trimethacrylate monomers and the like can be used as diluents to reduce the viscosity of the liquid polymerization medium. Typically, a dimethacrylate comonomer such as triethylene glycol dimethacrylate, commonly referred to as "TEGDM" is employed. Other suitable comonomeric methacrylates include ethylene glycol dimethacrylate, tetramethylene glycol dimethacrylate, trimethylol propyl trimethacrylate, 1,6-hexanediol dimethacrylate, 1,3-butanediol dimethacrylate, and the like.

In order to obtain an essentially color free dental restorative material, it is considered preferable to employ monomers and diluents which are substantially color-free exhibiting an APHA color range less than about 50 thereby appearing as clear and colorless as water.

The polymerization system also includes a visible light activated polymerization initiator such as benzil, diketones, dl-camphoroquinone (2,3-bornanedione), and the like. In addition, polymerization accelerators are employed in conjunction with the initiators. These accelerators are generally tertiary amines such as diethylaminoethyl acrylate, diethylamino ethylmethacrylate (commonly referred to as "DEA-EMA"), dimethylamino ethylmethacrylate, and the like.

Since such polymerization systems are activated by a visible light source, it is considered preferable to also include an ultraviolet absorber in the polymerization system in order to avoid discoloration of the resin from any incident ultraviolet light. Suitable UV absorbers are benzophenones, benzotriazoles, and the derivatives thereof such as TINUVIN P, a benzotriazole UV absorbent available from Ciba-Geigy Corporation, Ardsly, New York.

Typically, the polymerization system on a weight percent basis, comprises:
  50–60% Bis-GMA
  40–50% TEGDM
  0.5–5% Tinuvin P
  0.05–0.35% dl-camphoroquinone
  0.05–0.5% DEA-EMA
in specific amounts selected within the given ranges to yield a 100 percent by weight polymerization system.

Preferably, the polymerization system, on a weight percent basis,comprises,:
  52.5–57.5% Bis-GMA
  42.5–47.5% TEGDM
  0.75–1.5% Tinuvin P
  0.08–0.24% dl-camphoroquinone
  0.1–0.4% DEA-EMA
in specific amounts selected within the given ranges to yield a 100% by weight polymerization system.

It is considered preferable that each component of the polymerization system be selected from as high purity stocks as are commercially available since contaminants can give rise to cross reactions between the initiator and accelerator discoloring the final resin product.

The above unfilled monomeric system can be used per se, as a bonding agent for the filled composite resin system, of the present invention in the actual restoration process as set forth hereinafter.

If desired, the monomeric systems of the present invention can be tinted to any of the desired universal colors by incorporating in the unfilled monomeric system trace amounts of any FDA and FDC approved, low alumina dye, pigment, and lakolene (low dye ) preparations such as carbon black, yellow No. 5, yellow No. 6, and the like as well as mixtures thereof. The dye, pigment or lakolene preparations can be easily homogeneously dispersed within the unfilled monomeric system by ultrasonification or other mixing techniques thereby providing better color stability.

FILLED COMPOSITE RESTORATIVE PREPARATION

The filled composite restorative materials of the present invention can be prepared by admixing from about 20–30% by weight, preferably 20–26% by weight of the unfilled visible light-polymerizable monomeric methacrylic ester system prepared as described above with from about 65–79% by weight, preferably about 74–79% by weight of the treated inorganic filler and from about 1–5% by weight, preferably about 2% by weight of colloidal fumed silica. The fumed silica is of sub-micron particle size, generally exhibiting an average particle size of from about 0.01 to 0.05 micron. The use of colloidal fumed silica is important in that it introduces hydrophobicity to the resulting composite and thereby minimizes water sorption in the final composite to less than 0.7 mg/cm$^2$ as required of a type II resin by the American Dental Association Specification No. 27. In addition, the fumed silica contributes to better marginal integrity or adaptability and less marginal leakage. Also, handling characteristics such as bulk and consistency are improved. Flow and/or slump are minimized for better restoration placement in cavity preparations.

The colloidal fumed silica is preferably admixed with the organic monomeric system until a homogeneous mixture is obtained. Thereupon the treated inorganic filler is admixed therewith in a planetary mixer under vacuum to form a homogeneous paste. The resulting paste can be passed through a two roll stainless steel mill, if desired, to ensure homogeneity. The resulting paste can then be packaged in appropriate, essentially light free, packaging which permits easy dispensing-such as in, syringes.

RESTORATIVE DENTAL PROCEDURE

The visible light curable filled composites of the present invention are X-ray opaque and require no proportioning or mixing of components as was heretofore necessary with two-component paste systems.

The visible light curable filled composites of the present invention can be polymerized by exposure to a visible light source, e.g. a 150 watt halogen light source or any visible light source which is capable of generating visible light within wave lengths ranging from about 250 to about 750 nanometers, preferably from about 450 to 500 nanometers, and most preferably from about 468 to about 480 nanometers, for about 20 seconds.

For cavity preparation, one should use carbide friction-grip burs, cavo surface beveling i.e., Class V, is recommended to increase retention via greater enamel surface etching, to minimize marginal leakage and ultimately improve marginal adaptability.

Acid etching of the enamel can be effected by applying an aqueous orthophosphoric acid solution or gel containing about 35–40%, preferably 37% by weight, orthophosphoric acid to the enamel surface with a small cotton pellet. Care should be taken to avoid cavity preparations. Generally, use of a continuous slow and gentle application for 60 seconds on permanent teeth and 90 seconds on deciduous teeth is sufficient. Pressure should be avoided which would destroy the retentive characteristics of the etched surface. A visible layer of the acid solution should be present at all times during the etching. Additional solution may be required to maintain a visible layer. The acid solution should never be allowed to dry out on the tooth surface. After etching, the area should be well washed with water. A rubber dam can be appropriately placed in position to make sure that no acid is ingested by the patient during washing or gingival tissue irritated. Thereafter, the area should be dried thoroughly with warm, oil-free air. A properly etched tooth will have a dull, whitish appearance. For bonding and sealing Class I, III and V restorations, the enamel should, if possible be conditioned at least one millimeter beyond the margin of the cavity preparation. For Class IV restorations, the etched area should be at least as wide as the tooth structure being replaced, but never less than two millimeters.

The dry cavity preparation should be lined with any conventional calcium hydroxide preparation. Use of zinc oxide eugenol should be avoided. After the calcium hydroxide hardens, an extremely thin layer of bonding agent i.e., the unfilled monomeric system, should be applied over the etched enamel and the previously applied layer of calcium hydroxide. An extremely thin layer is obtained by removing the excess bonding agent from the enamel surface by a brush or similar means. The bonding agent is then polymerized by exposure to a visible light source for about 20 seconds. Thereafter, the filled composite resin of the present invention is placed into the cavity preparation while also assuring a proper featheredge extension thereof onto the etched enamel beyond the cavity margin or fracture line. In addition to manual shaping and contouring, strips and crown forms may be used to restore anatomic form and minimize the amount of excess to be removed. Matrix strips are recommended to contain and shape visible light cure compositions in appropriate cavity preparations, i.e. Class III, IV and V restorations.

Thereafter, each area of the restoration surface can be exposed to a suitable visible light source for at least 10 seconds. For Class III and IV restorations, the composite material should be additionally exposed to the visible light source through lingual or buccal enamel walls. Exposure times can usually vary between 10 and about 40 seconds. Complete curing and full strength are achieved within 24 hours. If desired, or necessary, the restored area can be trimmed with carbide aesthetic trimmers and subsequently with low grit diamonds and pre-polished and ultimately polished with green rubber wheels, caps, cones or Sof-Lex discs.

The filled composite system of the present invention is especially useful for caries, fractures, lesions, chipping, lengthening, restoring or reconstructing, modification of tetracycline stained teeth, cervical erosion, veneers and the like.

The following examples further illustrate the present invention. Unless otherwise stated, all percentages and parts are by weight.

EXAMPLE 1

Borosilicate glass rods, available from Corning Glass Works, Corning, New York, are cut into cylindrical form. The resulting cylinders are loaded into a 5 gallon glass carboy until the carboy is ½ filled. The carboy is then filled with water, sealed and tumbled at 175 rpm for 48 hours to condition the glass rods.

The conditioned borosilicate glass rods are recovered and loaded into a 5 gallon polyvinylidene fluoride lined grinding vessel adapted for combined oscillatory and vibratory motion. The grinding vessel is loaded with the glass rods until ¾ filled. Three kilograms of X-ray opaque barium silicate glass frit (Esschem T-3000 available from Esschem Corporation, Essington, Pa) having an average particle size diameter of 10 microns are added to the grinding vessel and then water is added to fill the grinding vessel. The vessel is then sealed and vibrated for 24 hours whereupon the barium silicate frit is ground to an average particle size diameter ranging between about 5-6 microns and sufficient borosilicate glass is abraded off the rods to provide a barium silicate borosilicate glass mixture comprising about 89% barium silicate and about 11% borosilicate glass.

Figure 1:
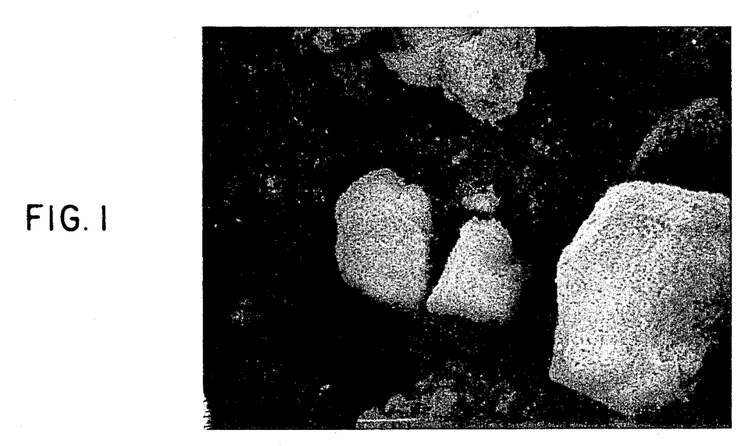
FIG. 1 is an electron photomicrograph of the inorganic filler after wet milling (250×)

The resulting aqueous slurry is recovered and strained through a series of 200, 400 and 600 mesh screens. The resulting filtrate is subjected to vacuum filtration and then dried in a convection oven at 120° C. for 24 hours. The dried, milled filler is recovered and crushed and ground with a mortar and pestle to a fine powder. The resulting milled filler is shown in FIG. 1 which illustrates the surface appearance of the wet milled barium silicate particles.

Figure 2:
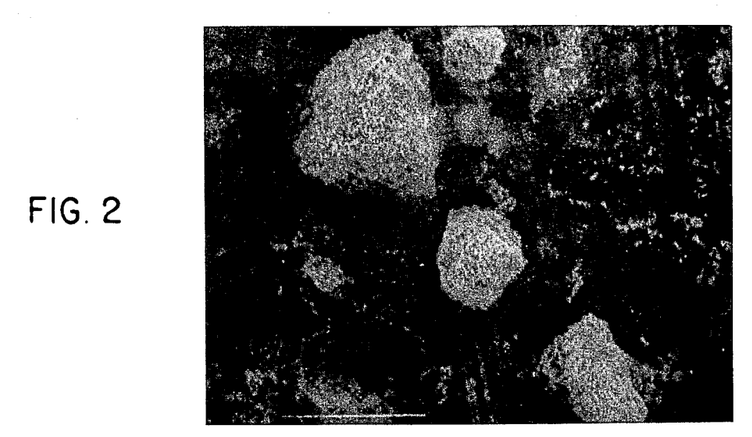
FIG. 2 is an electron photomicrograph of the inorganic filler of the present invention after buffered milling and etching at pH 12(250×)

Three kilograms of the dried, milled filler are charged to a glass carboy which is filled to one-half its volume with conditioned borosilicate glass rods prepared as described above. The carboy is then filled with six liters of a clear, colorless, aqueous solution of sodium hydroxide exhibiting a pH of 12 which is buffered with $Na_2HPO_4$. The loaded carboy is sealed and tumbled at 175 rpm for 4 hours. Thereafter, the resulting milled filler is recovered and subjected to vacuum filtration. The filter cake is washed with water until pH indicators in the filtrate indicate neutrality (pH=5.5-7.0) has been essentially obtained. The recovered filter cake is then dried in a convection oven at 120° C. for 24 hours. The neutralized filter cake is ground to a fine powder with a mortar and pestle. The resulting filler is shown in FIG. 2. It can readily be seen that milling with an aqueous etchant under controlled pH conditions imparts increased surface porosity to the barium silicate particles.

Figure 3:
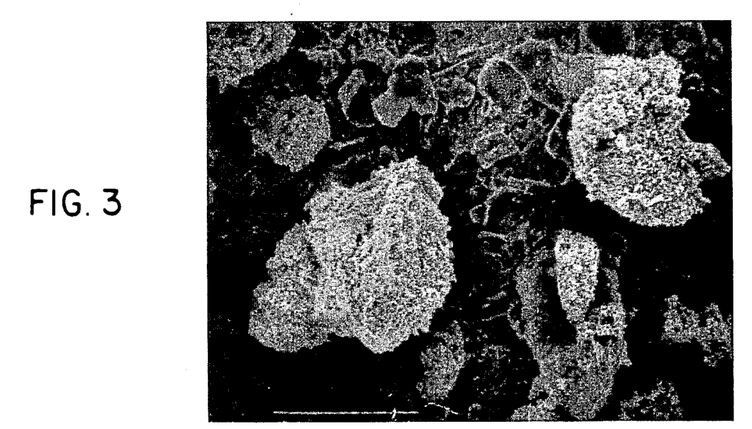
FIG. 3 is an electron photomicrograph of the inorganic filler of the present invention after silanizing milling (250×)

Silanization of the filler thus obtained is effected by filling a 5 gallon glass carboy to one-half its volume with borosilicate glass rods conditioned in the manner described hereinabove. Six kilograms of a solution of 8% silane in methanol is charged to the carboy along with 3 kilograms of the milled filler recovered from the aqueous etchant milling step. The carboy is sealed and tumbled for 6 hours at 175 rpm. The silanized slurry is recovered and subjected to vacuum filtration. The resulting filter cake is dried in a vacuum oven for one hour at 120° C. and then pulverized with mortar and pestle giving rise to silanized filler particles having an average particle size of 2.3 microns. Silanization results in 4.5% silane being coupled to the filler particles. The silanized filler particles are shown in FIG. 3. It can be seen that in addition to particle size reduction, the surface appearance of the filler particles undergo substantial surface modification with each milling operation.

100 grams of the monomeric matrix composition is prepared by admixing the following:
54.32 grams Bis-GMA
44.30 grams TEGDM
0.99 gram TINUVIN P
0.16 grams dl-camphorquinone
0.23 grams DEA-EMA A filled composite restoration material of the present invention especially suitable for anterior dental applications is prepared by admixing 24% by weight of the foregoing monomeric matrix composition with 74% by weight of the treated inorganic filler and 2% by weight of colloidal fumed silica having an average particle size of about 0.04 micron. The resulting composite is a homogeneous paste comprising the monomeric composition as the matrix with the treated inorganic filler and the fumed silica uniformly dispersed therein.

EXAMPLE 2

To demonstrate the surprising effect that controlled pH during milling with an aqueous etchant has on the diametral tensile strength (DTS) of inorganic filler particles prepared as described hereinabove, several samples of the filled composite resin of the present invention were prepared in identical manner except that a controlled pH was maintained at different pH levels during milling with an aqueous etchant—in this instance, NaOH.

DTS samples were prepared by curing the various samples of filled composite resin for 40 seconds with a SPECTRA-LITE visible light source available from Pentron Corporation, Wallingford, Connecticut. The samples were cured in a 6 mm. diameter×3 mm stainless steel split cylindrical mold, set on 25×75 mm glass microslides, condensed with a stainless steel spatula and covered with a glass cover micro slip 25×25 mm. The cured samples were immersed within 2 minutes of curing into a 37° C. ±0.1° C., 99.9±0.1% relative humidity, chamber for 15 minutes. Then the units were disassembled from the molds, polished with a 240 or finer silicon carbide strip, submerged in a chamber at 37° C.±0.1° C., 99.9.±0.1% relative humidity for 24 hours then subjected to diametral compression on an Instron machine at 1"/minute chart speed and 0.02"/minute cross head speed and then the pounds of load applied to cause fracture of the specimens were noted and employed to calculate the DTS. (DTS=$2P/\pi dl$ wherein P=load, d=specimen diameter and l=length of specimen).

As can be seen from the data below, a surprising increase in DTS is achieved by careful control of the pH during the controlled pH milling step. Most preferably, the pH is controlled to a pH of about 12 for the optimum results.

| pH | D.T.S. (psi) |
| --- | --- |
| 10 | 7750 |
| 11 | 8500 |
| 12 | 9310 |
| 13 | 7300 |

EXAMPLE 3

Employing the DTS testing procedure described in Example 2, a filled composite restorative material obtained in accordance with the present invention was compared to a competitive composite dental material filled with a filler having an average particle size of about 14.6 microns.

The filled composite material of the present invention exhibited a 24 hours DTS at 37° C.±0.1° C., 99.9±0.1% relative humidity, of 7663 psi (average of 6 specimens); whereas the competitive composite material exhibited a DTS of 4867 psi. (average of 6 specimens).

Figure 4:
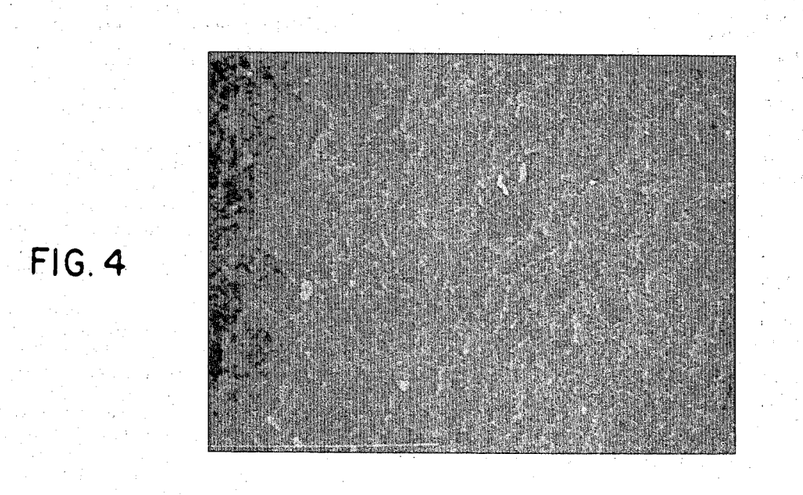
FIG. 4 is an electron photomicrograph of the fracture path obtained upon diametral tensile strength testing of the filled composite dental material of the present invention (500×)
Figure 5:
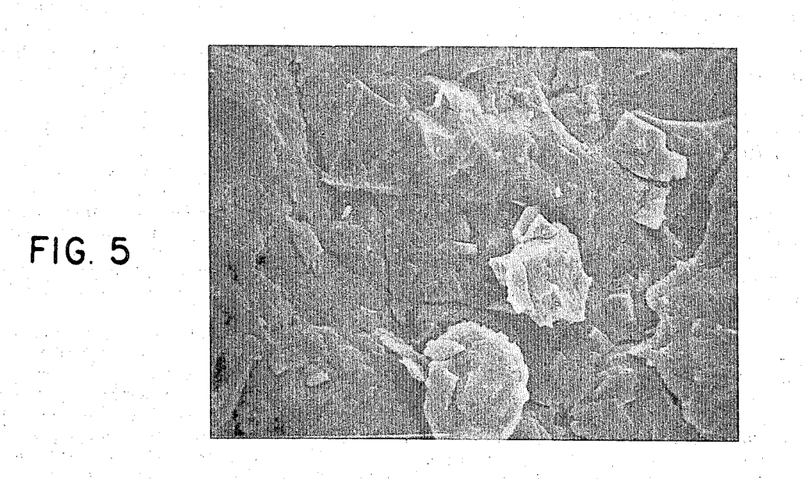
FIG. 5 is an electron photomicrograph of the fracture path obtained upon diametral tensile strength testing of a competitive composite dental material filled with large particle size filler and prepolymerized polymer blocks (microfilled) (500×).

Upon completion of D.T.S. testing, the fracture path obtained for each sample was observed using a scanning electron microscope at 500×. As can be seen by comparing FIG. 4, the fracture path obtained upon D.T.S. testing of the filled composite of the present invention, with FIG. 5, the fracture path obtained by D.T.S. testing of the competitive composite resin, the filled composite of the present invention exhibits a uniform particle distribution throughout the polymeric matrix and a uniform average particle size diameter of about 1–5 microns. In comparison, the large particles in the competitive composite are not uniformly dispersed in the matrix and can become easily dislodged therefrom thereby accounting for the substantial difference in D.T.S.

EXAMPLE 4

The immediate Barcol hardness/depth at 1, 2 and 3 millimeter depths for top/bottom was determined for both the filled composite resin of the present invention and the competitive composite dental material having an average particle size of about 14.6 microns. A GYZJ 935 Barcol Hardness Barber Colman portable impressor was employed. Samples of each material were cured for 40 seconds using a SPECTRA-LITE visible light source in 1 mm. 2 mm and 3 mm depth stainless steel molds of 10 mm. diameter set on 25×75 mm microglass slides and covered with 25×25 mm. cover glass. The average of 5 Barcol hardness measurements for each side top/bottom were noted. The results are summarized below.

| Sample | 1 mm Top | 1 mm Bottom | 2 mm Top | 2 mm Bottom | 3 mm Top | 3 mm Bottom |
| --- | --- | --- | --- | --- | --- | --- |
| Competitive material | 89.6 | 88.8 | 91.2 | 87.2 | 90.6 | 79.0 |
| Filled Composite of Present Invention | 95.4 | 96.0 | 95.2 | 94.8 | 94.6 | 91.6 |

From the foregoing, it can readily be seen that the composite of the present invention shows the greater top/bottom Barcol hardness and depth of cure uniformity at 1,2 and 3 mm. The superior uniformity in curing regardless of depth of cure obtained in accordance with the present invention is readily evident.

EXAMPLE 5

Both the composite resin of the present invention and the competitive filler composite material were tested for water sorption in accordance with the procedure set forth in the American Dental Association Specification No. 27 with the following results:

| Sample | Water Sorption after 1 week at 37° C. ± 0.1° C., 99.9 + 0.1% RH (mg/cm$^2$) |
| --- | --- |
| Competitive filled resin | 1.03 |
| Composite resin of present invention | 0.46 |

The excellent hydrophobicity of the filled composite resin of the present invention is readily evident.

EXAMPLE 6

A visible light curable dental restorative material especially suitable for posterior dental applications is prepared as follows:

Borosilicate glass rods, available from Corning Glass Works, Corning, New York, are cut into cylindrical form. The resulting cylinders are loaded into a 5 gallon carboy until the carboy is ½ filled. The carboy is then filled with water, sealed and tumbled at 175 rpm for 48 hours to condition the glass rods.

The conditioned borosilicate glass rods are recovered and loaded into a 5 gallon polyvinylidene fluoride lined grinding vessel adapted for combined oscillatory and vibratory motion. The grinding vessel is loaded with the glass rods until ¾ filled. Three kilograms of X-ray opaque barium silicate glass frit (Esschem T-3000 available from Esschem Corporation, Essington, Pa) having an average particle size diameter of 10 microns are added to the grnding vessel and then water is added to fill the grinding vessel. The vessel is then sealed and vibrated for 48 hours whereupon the barium silicate frit is ground to an average particle size diameter of about 3.2 microns and sufficient borosilicate glass is abraded off the rods to provide a barium silicate-borosilicate glass mixture comprising 80–85% barium silicate and 15–20% borosilicate glass.

The resulting aqueous slurry is recovered and strained through a series of 200, 400 and 600 mesh screens. The resulting filtrate is subjected to vacuum filtration and then dried in a convection oven at 120° C. for 24 hours. The dried, milled filler is recovered and crushed and ground with a mortar and pestle to a fine powder.

Three kilograms of the dried, milled filler are charged to a glass carboy which is filled to one-half its volume with conditioned borosilicate glass rods prepared as described above. The carboy is then filled with six liters of a clear, colorless, aqueous solution of sodium hydroxide exhibiting a pH of 12 which is buffered with $Na_2HPO_4$. The loaded carboy is sealed and tumbled at 175 rpm for 4 hours. Thereafter, the resulting milled filler is recovered and subjected to vacuum filtration. The filter cake is washed with water until pH indicators in the filtrate indicate neutrality (pH=5.5–7.0) has been essentially obtained. The recovered filter cake is then dried in a convection oven at 120° C. for 24 hours. The neutralized filter cake is ground to a fine powder with a mortar and pestle. The resultant average diameter particle size is about 2 microns.

Silanization of the filler thus obtained is effected by filling a 5 gallon glass carboy to one-half its volume with borosilicate glass rods conditioned in the manner described hereinabove. Six kilograms of a solution of 8% silane in methanol is charged to the carboy along with 3 kilograms of the milled filler recovered from the aqueous etchant milling step. The carboy is sealed and tumbled for 6 hours at 175 rpm. The silanized slurry is recovered and subjected to vacuum filtration. The resulting filter cake is dried in a vacuum oven for 1–4 hours at 60° C. or 1 hour at 120° C. and then pulverized with mortar and pestle giving rise to silanized filler particles having an average particle size of 0.90 microns. Silanization results in 2.0–2.5% silane being coupled to the filler particles.

100 grams of the monomeric matrix composition is prepared by admixing the following:
54.24 grams Bis-GMA
44.30 grams TEGDM
0.99 gram TINUVIN P
0.16 grams dl-camphorquinone
0.28 grams DEA-EMA A filled composite restoration material of the present invention especially suitable for anterior dental applications is prepared by admixing 23% by weight of the foregoing monomeric matrix composition with 75% by weight of the treated inorganic filler and 2% by weight of colloidal fumed silica having an average particle size of about 0.04 micron. The resulting composite is a homogeneous paste comprising the monomeric composition as the matrix with the treated inorganic filler and the fumed silica uniformly dispersed therein.

The overall mechanical, physical, optical and thermal properties are:

| | | | | | |
|---|---|---|---|---|---|
| 24 HRS. Diametral Tensile Strength | 9,000 psi | | | | |
| 24 HRS. Compressive Strength | 60,000 psi | | | | |
| 1 week water sorption | 0.46 mg/cm²/week | | | | |
| | Barcol Hardness vs. Depth of Cure | | | | |
| | 1 mm | | 2 mm | | 3 mm |
| | Top | Bottom | Top | Bottom | Top | Bottom |
| Immediate hardness: | 96.0 | 96.0 | 96.0 | 94.4 | 96.0 | 92.4 |
| After 5 min 37° C., 99% R.H.: | 96.6 | 96.0 | 96.6 | 95.2 | 96.0 | 93.4 |
| Linear Coefficient of Thermal Expansion (aged 1 week @ 37° C., 99% R.H) | 14.50 mm/mm/°C. $\times 10^{-6}$ | | | | |
| Surface Roughness After Polishing To Green Rubber Wheels | 0.05 µm (Ra = roughness average using Talysurf procilometer) | | | | |
| Average diameter particle size | 0.90 µm | | | | |
| Fiber wt. % | 77.20% | | | | |
| Volume fraction percent filler | 69.99% | | | | |
| Accelerated Pin on Disc Slide wear tester results | 0.1 µm/hr. | | | | |

The loading weight percent of the treated filler phase in this posterior composite is 77.2 weight percent with a resultant volume fraction of 69.99%. This high volume fraction ($V_f$) is due to the particle size reduction, hence greater surface area and greater amount of borosilicate incorporated during the milling processes of the present invention. The resultant product has a higher packaging factor efficiency and less thermomechanical degradation with thermal cycling (5°–55° C.) at the filler/resin interface due to variable linear coefficients of thermal expansion between the resin matrix and the dispersed filler phase. Tensile forces acting on a to be sheared/fracture surface are minimized due to crack propagation blunting.

The physical properties of the posterior restorative system of the present invention is significantly superior to other posterior restorative materials currently on the market. The high diametral tensile strength, volume fraction and low coefficient of thermal expansion of the composite coupled with the small particle size of the filler results in a composite affording a statistically significant decrease in wear or abrasion; hence, a more suitable product for Posterior Class I and II molar consisting restoration in stress bearing situations.

As shown from the foregoing examples, the filled composite restorative system provided by the present invention overcomes the deficiencies inherent in the use of large particle size fillers as heretofore employed. Moreover, the composites of the present invention do not exhibit the deficiencies characteristic of the use of microfilled systems; namely, low diametral tensile strength, high water sorption, high shrinkage and high thermal expansion upon curing. In addition, the composites of the present invention provide X-ray opacity, excellent optical properties, excellent polishability and full compliance with the requirements of the American Dental Association Specification No. 27, Type II.

What is claimed is:

1. In a dental restorative material comprising 20–30% by weight of a visible light polymerizable methacrylic ester monomeric system, from about 65–79% by weight of an inorganic filler and from about 1–5% by weight of collidal fumed silica; said inorganic filler having an average particle size diameter ranging from about 0.5 to 5 microns and said collidal fumed silica having an average particle size ranging from about 0.01 to about 0.05 micron, the improvement comprising subjecting the filler to a series of milling steps comprising (1) wet milling in aqueous medium having a pH of 5–7; (2) surface etch milling in an aqueous etchant medium and (3) a silanizing milling in a silane solution.

2. A dental restorative material as defined in claim 1 wherein the inorganic filler comprises a mixture of from about 5–20% by weight of borosilicate glass and from about 80–95% by weight of an alkali metal or alkaline earth metal silicate.

3. A dental restorative material as defined in claim 2 wherein the alkali metal or alkaline earth metal silicate is barium silicate.

4. A dental restorative material as defined in claim 1 wherein the inorganic filler is prepared by wet milling, milling in a buffered aqueous etchant medium at a pH ranging from about 10–13 and a silanizing milling.

5. A dental restorative material as defined in claim 1 wherein the aqueous etchant medium has a pH of about 12.

6. A dental restorative material as defined in claim 1 wherein the inorganic filler contains from about 1.5–6% weight silane coupled thereto.

7. A dental restorative material as defined in claim 1 wherein the visible light polymerizable methacrylic ester monomeric system comprises a cross-linking methacrylate monomer, a co-monomeric methacrylate diluent, a visible light activated polymerization initiator, and a polymerization accelerator.

8. A dental restorative material as defined in claim 7 wherein the visible light polymerizable methacrylic ester monomeric system additionally contains an ultraviolet absorber.

9. A dental restorative material as defined in claim 8 wherein the cross-linking methacrylate monomer is the monomeric reaction product of 4,4′-isopropylidenediphenol and glycidyl methacryalte.

10. A dental restorative material as defined in claim 8 wherein the diluent within the visible light polymerizable methacrylic ester monomeric system comprises triethylene glycol dimethacrylate.

11. A dental restorative material as defined in claim 8 wherein the visible light polymerizable methacrylic ester monomeric system contains a visible light activated polymerization initiator comprising dl-camphoroquinone.

12. A dental restorative material as defined in claim 8 wherein the visible light polymerizable methacrylic ester monomeric system contains a polymerization accelerator comprising diethylaminoethylmethacrylate.

13. A dental restorative material as defined in claim 8 wherein the visible light polymerizable methacrylic ester monomeric system contains a benzotriazole ultraviolet absorber.

14. A dental restorative material as defined in claim 8 which is additionally tinted by incorporating therein a dye, pigment or lakolene preparation.

15. A dental restorative material as defined in claim 1 wherein the aqueous etchant medium is an aqueous solution of a base maintained at a pH ranging from about 10–13.

16. A dental restorative material as defined in claim 1 wherein the inorganic filler comprises a mixture of about 89% barium silicate and about 11% borosilicate glass having about 2.5% silane coupled thereto, said inorganic filler having an average particle size of about 2.3 microns.

17. A dental restorative material as defined in claim 16 wherein 74% by weight of said inorganic filler and 2% by weight of colloidal fumed silica having an average particle size of about 0.04 microns are admixed with 24% by weight of a monomeric matrix composition comprising about
54.32 wt. % of the monomeric reaction product of 4,4′-isopropylidendiphenol and glycidyl methacrylate
44.30 wt. % triethylene glycol dimethacrylate
0.99 wt. % benzotriazole
0.16 wt. % dl-camphorquinone
0.23 wt. % diethylamino-ethylmethacrylate.

18. A dental restorative material as defined in claim 1 wherein the inorganic filler comprises a mixture of 80–85% barium silicate and 15–20% borosilicate glass having about 2.0–2.5% silane coupled threto, said inorganic filler having an average particle size of about 0.90 microns.

19. A dental restorative material as defined in claim 18 wherein 75% by weight of said inorganic filler and 2% by weight of colloidal fumed silica having an average particle size of about 0.04 micron are admixed with 23% by weight of a monomeric matrix composition comprising about
54.27 wt. % of the monomeric reaction product of 4,4′-isopropylidenediphenol and glycidyl methacrylate
44.30 wt. % triethylene glycol dimethacrylate
0.99 wt. % benzotriazole
0.16 wt. % dl-camphorquinone
0.28 wt. % diethylamino-ethylmethacrylate.

* * * * *